Figure 1:
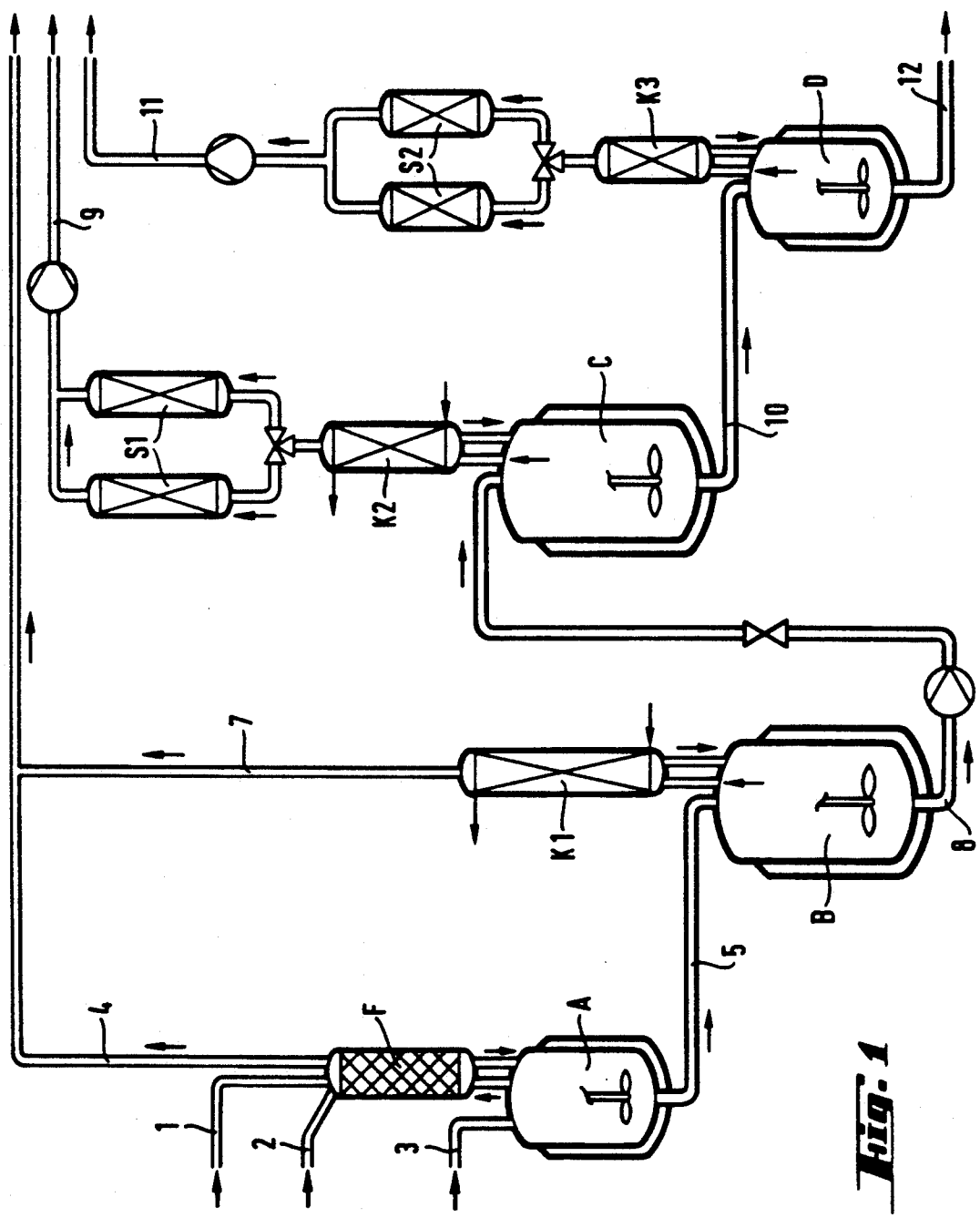

United States Patent [19]
Maul et al.

[11] Patent Number: 5,235,086
[45] Date of Patent: Aug. 10, 1993

[54] PROCESS FOR THE PREPARATION OF TRIS(2,4-DITERT-BUTYLPHENYL)-PHOSPHITE

[75] Inventors: Rudolf Maul, Lorsch/Hessen; Volker Schenk, Bensheim, both of Fed. Rep. of Germany

[73] Assignee: Ciba-Geigy Corporation, Ardsley, N.Y.

[21] Appl. No.: 759,987

[22] Filed: Sep. 16, 1991

Related U.S. Application Data

[63] Continuation of Ser. No. 563,769, Aug. 7, 1990, abandoned.

[30] Foreign Application Priority Data

Aug. 15, 1989 [CH] Switzerland .......................... 2975/89

[51] Int. Cl.$^5$ .............................................. C07F 9/145
[52] U.S. Cl. ......................................... 558/95; 558/96
[58] Field of Search ................................ 558/95, 96

[56] References Cited

U.S. PATENT DOCUMENTS

| | | | |
|---|---|---|---|
| 3,823,207 | 7/1974 | Herzog et al. | 260/976 |
| 4,276,233 | 6/1981 | Markezich et al. | 260/937 |
| 4,312,818 | 1/1982 | Maul et al. | 260/976 |
| 4,440,696 | 4/1984 | Maul et al. | 260/976 |
| 4,492,661 | 1/1985 | Maul et al. | 558/96 |

FOREIGN PATENT DOCUMENTS 2944254 5/1980 Fed. Rep. of Germany.
2940620 4/1981 Fed. Rep. of Germany.

*Primary Examiner*—Mary C. Lee
*Assistant Examiner*—Michael G. Ambrose
*Attorney, Agent, or Firm*—Luther A. R. Hall

[57] ABSTRACT

A process for the preparation of tris-(2,4-ditert-butylphenyl) phosphite from 2,4-ditert-butylphenol and phosphorus trichloride in the presence of catalysts, which comprises carrying out the reaction in an at least three-stage process in which the 2,4-ditert-butylphenol and 40-100% of the catalyst are combined in a preliminary stage and are brought together with the phosphorus trichloride in a first stage, these being allowed to react under normal pressure and at temperatures of 55° to 70° C. for a dwell time of 15 to 40 minutes, the reaction mixture is then reacted in a second stage under normal pressure and at temperatures of over 140° C., remaining amounts of catalyst being added to the first and/or second reaction stage, the reaction mixture is then kept under reduced pressure at temperatures of at least 186° C. in a third reaction stage, and the tris-(2,4-ditert-butylphenyl) phosphite is then isolated from the reaction mixture, the process being carried out in the absence of solvents.

14 Claims, 2 Drawing Sheets

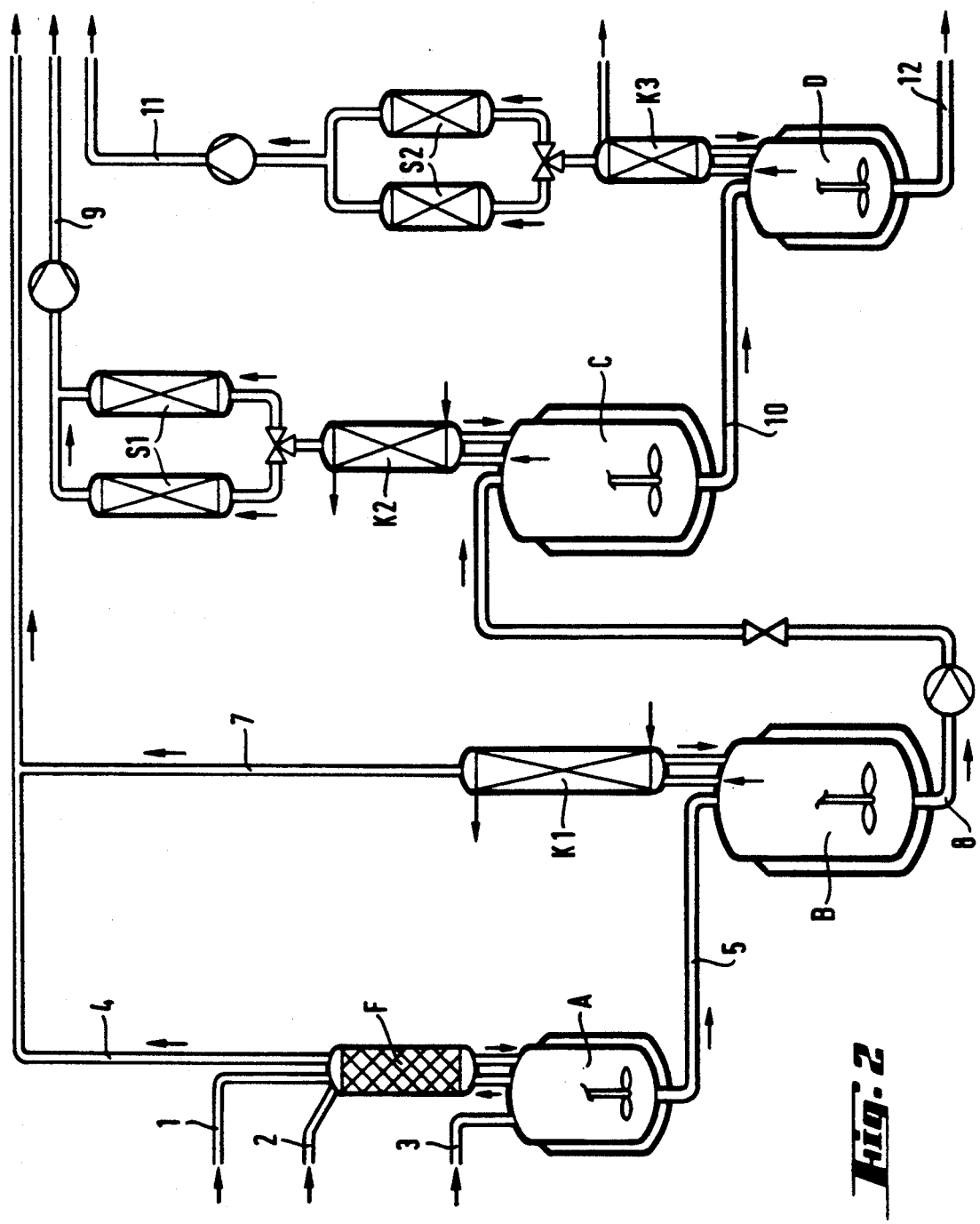

PROCESS FOR THE PREPARATION OF TRIS(2,4-DITERT-BUTYLPHENYL)PHOSPHITE

This is a continuation of application Ser. No. 563,769, filed on Aug. 7, 1990, now abandoned.

The invention relates to a process for the preparation of tris-(2,4-ditert-butylphenyl) phosphite from 2,4-ditert-butylphenol and phosphorus trichloride in the presence of a catalyst.

It is known from DE-A 2,007,070 to prepare triaryl phosphites from phenols and phosphorus trichloride, the reaction taking place in three stages in successive sections of equipment. The process can be operated in the absence of solvent, but problems then arise with the formation of foam in the reaction mixture to the point where the orderly course of the reaction is interfered with. A process is known from EP-A 0,000,757 for the preparation of triaryl phosphites by reacting phosphorus trihalides with hydroxyaromatic compounds in the presence of catalysts. According to Example 4 of EP-A 0,000,757 tris-(2,4-ditert-butylphenyl) phosphite can be prepared with the concomitant use of a solvent. Working with a solvent has the advantage that the course of the reaction and hence also the undesirable foam formation can be controlled, but has, in turn, the obvious disadvantage that the solvent, by its volume, reduces the space/time yield and has to be heated and cooled with the reactants and, at the end of the process, removed and worked up.

The object of the present invention was to avoid the said disadvantages and to provide a process which makes it possible to prepare tris-(2,4-ditert-butylphenyl) phosphite in a simple manner and in high space/time yields.

In accordance with the invention this is achieved by means of a process which comprises carrying out the reaction in an at least three-stage process in which the 2,4-ditert-butylphenol and 40–100% of the catalyst are combined in a preliminary stage and are brought together with the phosphorus trichloride in a first stage, these being allowed to react under normal pressure and at temperatures of 55° to 70° C. for a dwell time of 15 to 40 minutes, the reaction mixture is then reacted in a second stage under normal pressure and at temperatures of over 140° C., remaining amounts of catalyst being added to the first and/or second reaction stage, the reaction mixture is then kept under reduced pressure at temperatures of at least 186° C. in a third reaction stage, and the tris-(2,4-ditert-butylphenyl) phosphite is then isolated from the reaction mixture, the process being carried out in the absence of solvents.

The following embodiments, independently of one another, are preferred: for example, that the reaction mixture is subjected to a fourth stage, the reaction mixture being kept in the fourth stage at at least 186° C. and under reduced pressure, preferably a pressure of 6 to 20 hPa; that a reaction time of 45 to 75 minutes is maintained in the second stage; that a reaction time of 1.5 to 2.5 hours is maintained in the third stage; that a reaction time of 20 to 120 minutes is maintained in the fourth stage; and that a temperature of 190° to 195° is maintained in the fourth stage.

In a preferred embodiment of the process the 2,4-ditert-butylphenol is added in a 1-fold to 1.1-fold stoichiometric amount, relative to phosphorus trichloride.

Examples of catalysts available for the process according to the invention are those described in EP-A 0,000,757.

Examples of catalysts of this type are compounds belonging to the group comprising amines or ammonium salts, amides of carboxylic acids or of carbonic acid, non-aromatic N-containing heterocyclic compounds and salts thereof, primary, secondary and tertiary phosphines and salts thereof or esters of phosphoric acids and phosphonic acids.

The amines and ammonium salts, amides and nitrogen-containing heterocyclic compounds or phosphines can contain, as substituents, alkyl, cycloalkyl, aryl, particularly phenyl, alkaryl, particularly alkylated phenyl, aralkyl, particularly benzyl, or alkaralkyl, particularly alkylated benzyl, groups which preferably contain 1 to 18 C atoms, particularly 1 to 12 C atoms, and are interrupted, if appropriate, by oxygen or sulfur atoms. Alkyl contains especially 1 to 6 C atoms and cycloalkyl is especially cyclopentyl and cyclohexyl.

The catalysts to be used in the form of salts are preferably the halides and particularly the chlorides. The salts can also be formed in situ by means of the hydrogen halide formed in the course of the process. Nevertheless, it is advantageous in certain cases to employ the salts themselves as catalysts. The amines and ammonium salts comprise one catalyst group. These can be primary, secondary and tertiary amines and also salts thereof. The salts also include the quaternary ammonium salts. The secondary amines, their salts and the quaternary ammonium salts are preferred. The alkyl-substituted and cycloalkyl-substituted amines or ammonium salts are preferred.

The following are examples: methylamine, ethylamine, propylamine, n-butylamine, t-butylamine, pentylamine, octylamine, dodecylamine, phenylamine, benzylamine, dimethylamine, diethylamine, methylethylamine, methylbutylamine, methyoctylamine, methylphenylamine, ethylbenzylamine, trimethylamine, triethylamine, tributylamine, octyldimethylamine and dimethylphenylamine and also tetramethylamonium, trimethylethylamonium, triethylmethylamonium, tributylmethylamonium, tetrabutylamonium, trimethyloctylamonium, triphenylmethylamonium and tribenzylmethylammonium chloride, bromide or iodide. Examples of other ammonium salts are methylammonium, octylammonium, dimethylammonium, methylcyclohexylammonium, dibenzylammonium, diphenylammonium, trimethylammonium, tributylammonium, tribenzylammonium and triphenylammonium chloride, bromide and iodide. The amines and ammonium salts can also contain aromatic N-heterocyclic radicals, for example pyridyl. These amines are more effective than the purely aromatic N-heterocyclic compounds.

The amides of carboxylic acids constitute another group of catalysts. This group also includes the ureas and their bisurea derivatives. The amides can be derived from polyfunctional, preferably monofunctional, carboxylic acids containing, in particular, 1 to 14 C atoms. The amides can also be derived from aromatic N-heterocyclic compounds. Cyclic amides, for example $\epsilon$-caprolactam, are also suitable. The amides derived from carboxylic acids preferably have the formula

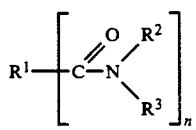

in which, if n=1, $R^1$ is phenyl, benzyl, naphthyl, cyclohexyl, cyclopentyl, pyridyl, hydrogen or alkyl having 1 to 13, preferably 1 to 6, C atoms, if n=2, $R^1$ is phenylene, naphthylene, cyclohexylene or alkylene having 1 to 12, preferably 1 to 6, C atoms or a direct bond, and $R^2$ and $R^3$ independently of one another are a hydrogen atom, phenyl, benzyl, cyclohexyl and alkyl having 1 to 12, preferably 1 to 6, C atoms or $R^2$ and $R^3$ together are alkylene which preferably has 4-7 C atoms and, if appropriate, is interrupted by O or S atoms. Examples are formamide, oxamide, dimethylformamide, acetamide, N,N-dimethylacetamide, picoanilide, benzamide, terephthalamide and trimellitamide. Dimethylformamide is very particularly preferred as the catalyst in the present process.

The following, besides urea, may be mentioned as examples of amides of carbonic acid: tetramethylurea, diphenylurea, dibenzylurea, diethylurea, di-n-octylurea and bisurea derivatives, for example ethylenebisurea. Examples of cyclic ureas are hydantoin and benzimidazolone.

Non-aromatic N-heterocyclic compounds constitute another group of catalysts suitable for the process according to the invention. These can contain 1 to 3N atoms and, if appropriate, one or 2 O and S atoms. They can also be unsaturated. They can be present in the form of salts and also in the form of quaternary ammonium bases, and the N atoms can be substituted, preferably by alkyl groups having 1 to 12 C atoms. The following are examples: pyrrolidine, $\Delta^3$-pyrroline, N-methylpyrrolidine, dihydroindole, pyrazolidine, imidazolidine, $\Delta^2$-pyrazoline, 1-phenylpyrazolidine, oxazolidine, thiazolidine, oxazoline, triazolidine, oxadiazolidine, thiadiazolidine, piperidine, morpholine, N-methylmorpholine, quinolidine, 1,2-dihydropurine, 8-aza-bicyclo-(3,2,1)-octane, piperazine and N-methylpiperazine.

The primary, secondary and tertiary phosphines and salts thereof constitute another group of catalysts to be used in accordance with the invention. The tertiary phosphines and their salts are preferred, amongst the salts the hydrohalides, preferably the hydrochlorides, hydrobromides and hydriodides. The phosphorus atom can be unsubstituted or substituted by phenyl, benzyl, cyclohexyl and/or alkyl having 1 to 12, preferably 1 to 6, C atoms. The following are examples: methylphosphine, ethylphosphine, hexylphosphine, dodecylphosphine, dimethylphosphine, ethylmethylphosphine, diphenylphosphine, dicyclohexylphosphine, dibenzylphosphine, phenylmethylphosphine, triphenylphosphine, tribenzylphosphine, tricyclohexylphosphine, trimethylphosphine, triethylphosphine, tripropylphosphine, tributylphosphine, triisobutylphosphine, tripentylphosphine, trihexylphosphine and dimethylphenylphosphine and hydrochlorides, hydrobromides and hydiodides thereof.

In the case of the esters of phosphoric acid and phosphonic acid the alcohol radicals are preferably derived from phenols, and especially, $C_1$-$C_{18}$alkanols and cycloalkanols, for example from phenol, 2-methylphenol, cyclohexanol, methanol, ethanol, propanol, butanol, hexanol, octanol, i-octanol, dodecanol and octadecanol.

The following are examples of phosphonic acids: phenylphosphonic, benzylphosphonic, cyclohexylphosphonic, methylphosphonic, ethylphosphonic, propylphosphonic, butylphosphonic, pentylphosphonic and hexylphosphonic acid.

The catalyst can be employed in amounts of, for example, 0.005 to 10 mol-%, appropriately in amounts of 0.05 to 8 mol % and preferably of 4 to 6 mol %, in each case relative to the phosphorus trichloride.

The process according to the invention is carried out in apparatus known per se. Reaction vessels in the form of stirred kettles are particularly appropriate and reaction vessels in the form of reaction columns, particularly with inserts which force intimate mixture on the reactants by means of circuitous paths are also possible.

A heatable reaction vessel equipped with at least two inlets, one outlet and a stirring device are appropriately envisaged for carrying out the first stage of the process. The phosphorus trichloride is preferably introduced directly into the reaction vessel via one inlet, the 2,4-di-tert-butylphenol through a column, for example a packed column, and through the second inlet. Depending on its nature, the catalyst can be introduced into the reaction vessel in part separately via a third inlet. 40-100% of the catalyst are put into the second inlet, also via the packed column. The streams of starting materials are appropriately controlled in such a way that the phosphorus trichloride is taken initially and the catalyst and the phenol compound reach the reaction vessel via the packed column. The HCl formed during the reaction which sets in escapes through the packed column countercurrent to the phenol compound. Entrained phosphorus trichloride is absorbed by the phenol compound and recycled into the reaction vessel. The reaction is already catalysed by the catalyst which is present in the column at the same time, and the escaping phosphorus trichloride reacts with the phenol compound which flows through the column. Thus a preliminary step already takes place in the column. The reaction mixture then flows into the first reaction vessel. The reactants can be intimately mixed in the reaction vessel by means of a stirring device. At the same time the reaction mixture is heated to temperatures of 55° to 70° C. Temperatures of 60° to 70° C. are preferred. The HCl formed in the reaction is removed via the packed column and is disposed of. The first stage of the reaction is complete after 15 to 40 minutes. It is then possible to carry out the second stage of the reaction in the first reaction vessel, but preferably the contents of the reaction vessel from the first stage are transferred into a second reaction vessel, preferably a heatable stirred kettle. This stirred kettle preferably has feed inlets for the reaction mixture from the vessel of the first stage and, if appropriate, for the addition of a second part amount of the catalyst, and also has a gas outlet equipped with a reflux condenser for discharging the HCl formed during second reaction stage. The second stirred kettle is also preferably equipped with a stirring device. When the second stage starts the reaction mixture is immediately heated to over 140° C., for example 145° to 200° C., preferably 150° to 170° C. and particularly preferably about 160° C., and is preferably kept at these elevated temperatures for 45 minutes to 75 minutes, preferably 60 minutes. When the second stage is complete, the reaction mixture is subjected to the third stage either in the same reaction vessel or, preferably, in another reaction vessel. The heatable reaction vessel for the third stage is preferably equipped with an inlet for the reaction mixture, an outlet for reactants which escape in the form of gas, an outlet for the reaction mixture and, preferably, a stirring device. The outlet for the reactants which are evolved, in particular HCl, can have a reflux condenser and, if appropriate, also a desublimer in order to separate the escaping reactants. Furthermore, since the third stage is carried out under reduced pressure, appropriate arrangements are provided, such as a vacuum pump and appropriate seals and valves. The third stage of the reaction is carried out at at least 186° C., appropriately at 186° C. to 210° C. and preferably at 190° to 195° C., under a reduced pressure of, appropriately, 10 to 60 hPa, in particular 10 to 20 hPa and preferably 15 hPa. The reaction time for the third stage is, for example, 1 to 2.5 hours, preferably 2 hours. After the expiry of the reaction time the reaction mixture is, if desired, subjected to the fourth stage. This is effected either by bringing the reaction mixture into the reaction vessel of the third stage or, preferably, bringing it into another reaction vessel and subjecting it to the conditions of the fourth stage in this other reaction vessel, which can be heated and evacuated. The reaction mixture is also preferably stirred in the fourth stage. The reaction vessel of the fourth stage should therefore contain not only an inlet for the reaction mixture but also a stirring device and a suitable outlet for removing, in particular, the gaseous products of the reaction, preferably an outlet containing a reflux condenser and a desublimer. Finally, a suitable outlet should be provided at this reaction vessel for discharging the reaction material. Since the fourth stage is to be carried out under reduced pressure, appropriate means of producing a vacuum and seals should be provided. The reaction mixture is appropriately subjected to the fourth stage for 20 to 120 minutes, preferably 60 minutes. Meanwhile the pressure can be, for example, 6 to 20 hPa, appropriately 10 to 15 hPa and preferably 10 hPa. The temperature in this fourth stage is at least 186° C., appropriately 186° C. to 210° C. and especially 190° to 195° C.

It is possible to distill off the 2,4-ditert-butylphenol which may be used in excess from the reaction vessel of the third stage or, if used, the fourth stage, and, if desired, to recycle it to the reaction. The excess 2,4-ditert-butylphenol can also be disposed of from the reaction mixture of the third stage or, if used, the fourth stage.

A preferred embodiment consists in carrying out the process of the present invention in a three-stage kettle cascade.

The particularly preferred embodiments of the present invention include carrying out the process in a four-stage kettle cascade.

Another preferred embodiment is to stir the reaction mixture in at least one stage.

It is very particularly preferable to stir in all four stages.

It is also preferable in the present process to maintain a temperature of 170° to 190° C. in the second stage.

Another preference in the process of the invention is to maintain a temperature of 190° to 195° C. in the third and the fourth stage, independently of one another.

In the process according to the invention the amount of catalyst envisaged is added to the reaction to the extent of 40 to 100% through the packed column in which the preliminary stage described above is carried out. It is appropriate to add 50 to 100%, preferably 70 to 100% and especially 90 to 100%, of the catalyst to the reaction via the packed column.

Remaining amounts of catalyst, insofar as not fed in via the packed column, are added in the first and/or second stage of the reaction.

Remaining amounts of catalyst, unless 100% of the catalyst are added to the reaction via the packed column, are preferably added to the first reaction stage.

It is very particularly preferable to add the whole amount of catalyst, i.e. 100% of the catalyst, to the reaction via the packed column. All percentage figures relate to weight.

The continuous mode of operation is particularly preferred for the process according to the invention.

The present process according to the invention has the advantage that tris-(2,4-ditert-butylphenyl) phosphite, which, in terms of processes, can only be obtained with difficulty, can be obtained in a high space/time yield. As a result of dispensing with a solvent more reaction volume is available in the present process, which makes higher reaction temperatures and hence higher reaction rates possible, and the heating up times and the time needed for distilling off the solvent prior to the further working up, in particular the crystallization, of the product are omitted.

The processes of the state of the art quoted initially are incapable of giving satisfaction in this respect, since it is absolutely necessary to use a solvent for the compound of present interest, tris-(2,4-ditert-butylphenyl) phosphite, by virtue of its high melting point.

EXAMPLE AND DESCRIPTION OF THE DRAWINGS

The following flows of materials:

| Addition of | | g/hour | Addition to |
|---|---|---|---|
| 2,4-ditert-butylphenol, 98.9% pure | [1] | 994 | via packed column (F) into reactor (A) |
| Phosphorus trichloride | [3] | 216.2 | Reactor (A) |
| Dimethylformamide (catalyst) | [2] | 6 | via packed column (F) into reactor (A) | are set up in a four-stage stirred kettle cascade such as can be seen from the diagram (FIG. 1), composed of a) a reactor (A) having a packed column (F) for the first stage, b) a main reactor (B) equipped with a reflux condenser (K1) for the second stage, c) a second main reactor (C) equipped with a reflux condenser (K2) and after that a desublimer (S1) for the third stage, and finally d) an after-reactor (D) equipped with a reflux condenser (K3) and a desublimer (S2).

a) Conditions in reactor (A):

Normal pressure, temperature 65° C., dwell time 30 minutes, discharge of 89.8 g/hour of HCl [4] via the packed column (F) to waste disposal and discharge of 1126.4 g/hour of reaction mixture [5] via the bottom valve to the first main reactor (B).

b) Conditions in the first main reactor (B):

Normal pressure, temperature 165° C., dwell time 1 hour, discharge of 64 g/hour of HCl [7] via a reflux condensder (K1) and discharge of 1062.4 g/hour of reaction mixture [8] via the bottom valve to the second main reactor (C).

c) Conditions in the second main reactor (C):

Reduced pressure 15 hPa, temperature 190° C., dwell time 2 hours, discharge of 13 g/hour of HCl [9] via a reflux condenser (K2) and a desublimer (S1) and discharge of 1049.4 g/hour of reaction mixture [10] via the bottom valve into the after-reactor (D).

d) Conditions in the after-reactor (D):

Reduced pressure 10 hPa, temperature 190° C., dwell time 60 minutes, discharge of 5.4 g/hour of HCl [11] via a reflux condenser (K3) and a desublimer (S2) and discharge of 1045 g/hour of reaction mixture [12] containing 1003.2 g/hour of tris-(2,4-ditert-butylphenyl) phosphite, to be crystallized.

The end product is of high purity, and virtually no content of monochloro and dichloro compounds or unreacted PCl$_3$ could be detected.

FIG. 2 shows an alternative embodiment differing from the embodiment described above in that the reflux condenser (K3) also constitutes a distillation device in which the excess 2,4-ditert-butylphenol can be removed. This 2,4-ditert-butylphenol can be recycled to the reaction via the feed inlet [1].

What is claimed is:

1. An improved process for the preparation of tris(2,4-di-tert-butylphenyl) phosphite by an at least three stage process from 2,4-di-tert-butylphenol and phosphorus trichloride in the presence of a catalyst selected from the group consisting of an amine, ammonium salt, amide of a carboxylic acid, amide of a carbonic acid, non-aromatic N-containing cyclic compound, salt of non-aromatic N-containing cyclic compound, primary phosphine, secondary phosphine, tertiary phosphine, salt of a phosphine, ester of phosphoric acid and ester of phosphonic acid, wherein the improvement comprises carrying out the reaction in the absence of a solvent by
   (i) combining 2,4-di-tert-butylphenol and 40-100% of the catalyst;
   (ii) introducing the 2,4-di-tert-butylphenol into the reaction vessel containing phosphorus trichloride in a 1-fold to 1.1-fold stoichiometric amount relative to the phosphorus trichloride, and allowing them to react under normal pressure and at a temperature of 55° to 70° C. with a dwell time of 15 to 40 minutes;
   (iii) reacting the mixture under normal pressure at a temperature of over 140° C., the remaining amounts of catalyst being added during steps (ii) or (iii) or both (ii) and (iii);
   (iv) keeping the reaction mixture under reduced pressure at a temperature of at least 186° C.; and
   (v) isolating tris(2,4-di-tert-butylphenyl) phosphite from the reaction mixture.

2. A process according to claim 1, wherein the reaction mixture is subjected to an additional stage in which the reaction mixture is kept at at least 186° C. and under reduced pressure.

3. A process according to claim 1, wherein a reaction time of 45 to 75 minutes is maintained in stage (iii).

4. A process according to claim 1, wherein a reaction time of 1.5 to 2.5 hours is maintained in stage (iv).

5. A process according to claim 2, wherein a reaction time of 20 to 120 minutes is maintained in stage the additional ahead of stage.

6. A process according to claim 2, wherein a temperature of 190° to 195° C. is maintained in stage the additional ahead of stage.

7. A process according to claim 1, wherein the process is carried out in a three-stage kettle cascade.

8. A process according to claim 2, wherein the process is carried out in a four-stage kettle cascade.

9. A process according to claim 1, wherein the reaction mixture is stirred in at least one stage.

10. A process according to claim 1, wherein a temperature of 150° to 170° C. is maintained in stage (iii).

11. A process according to claim 1, wherein a temperature of 190° to 195° C. is maintained in stage (iv).

12. A process according to claim 1, wherein stage (iv) is carried out under a reduced pressure of 10 to 60 hPa.

13. A process according to claim 1, wherein 50-100% of the amount of catalyst employed and the 2,4-ditert-butylphenol are added to the reaction via a packed column in which stage (i) is carried out.

14. A process according to claim 1, wherein the process is carried out continuously.

* * * * *